United States Patent [19]

Beck

[11] Patent Number: 6,107,294
[45] Date of Patent: Aug. 22, 2000

[54] THIAZOLO[4,5-D]PYRIMIDINES AND PYRIDINES AS CORTICOTROPIN RELEASING FACTOR (CRF) ANTAGONISTS

[75] Inventor: James Peter Beck, Smyrna, Del.

[73] Assignee: Dupont Pharmaceuticals, Wilmington, Del.

[21] Appl. No.: 09/283,373

[22] Filed: Mar. 31, 1999

Related U.S. Application Data

[60] Provisional application No. 60/080,537, Apr. 3, 1998.
[51] Int. Cl.$^7$ ...................... C07D 513/04; A61K 31/519; A61K 31/53
[52] U.S. Cl. .......................... 514/241; 514/258; 544/255; 544/215
[58] Field of Search ..................... 544/255, 215; 514/258, 241

[56] References Cited

FOREIGN PATENT DOCUMENTS

| | | |
|---|---|---|
| 0778277 A1 | 6/1997 | European Pat. Off. . |
| 95/33750 | 12/1995 | WIPO . |
| 98/08847 | 3/1998 | WIPO . |

OTHER PUBLICATIONS

J.E. Morley, et al., Neuropeptides: Conductors of the Immune Orchestra, *Life Sciences*, 41, 527–544, 1987.
C.B. Nemeroff, et al., Elevated Concentrations of CSF Corticotropin–Releasing Factor–Like Immunoreactivity in Depressed Patients, *Science*, 226, 1342–1344, Dec. 14, 1984.
George F. Koob and Karen T. Britton, Behavior Effects of Corticotropin–Releasing Factor, Corticotropin–Releasing Factor: Basic and Clinical Studies of Neuropeptide, CRC Press, 253–265, 1990.
C.W. Berridge and A.J. Dunn, A Corticotropin–Releasing Factor Antagonist Reverses the Stress–Induced Changes of Exploratory Behavior in Mice, *Hormones and Behavior*, 21, 393–401, 1987.
E.B. De Souza et al., Corticotropin–Releasing Facotr Receptors are Widely Distributed with the Rat Central Nervous System . . . , *The Journal of Neuroscience*, 5, 3189–3203, Dec. 1985.
P.W. Gold et al, Psychiatric Implications of Basic and Clinical Studies with Corticotropin–Releasing Factor, *The American Journal of Psychiatry*, 141, 619–627, May 1984.
Jean Rivier, et al., Characterization of Rat Hypothalamic Corticotropin–Releasing Factor, *Proc. Natl. Acad. Sci. USA*, 80, 4851–4855, Aug. 1983.
G.F. Koob, Stress, Corticotropin–Releasing Factor, and Behavior, *Perspectives and Behavioral Medicine*, 2, 39–52, 1985.
P.W. Gold et al, Responses to Corticotropin–Releasing Hormone in the Hypercortisolism of Depression and Cushing's Disease, *New England Journal of Medicine*, 314, 1329–1335, May 22, 1986.

Adrian J. Dunn and Craig W. Berridge, Physiological and Behavioral Responses to Corticotropin–Releasing Factor Administration: . . . , *Brain Research Reviews*, 15, 71–100 1990.
J. Edwin Blalock, A Molecular Basis for Bidirectional communication Between the Immune and Neuroedocrine Systems, *Physiological Reviews*, 69, 1–32, Jan. 1989.
Dimitri E. Grigoriadis, et al., Effects of Chronic Antidepressant and Benzodiazepine Treatment on Corticotropin–Releasing–Factor Receptors in Rat Brain and Pituitary, *Neuropsychopharmacology*, 2, 53–60, 1989.
Florian Holsboer, et al., Acth and Multisteroid Responses to Corticotropin–Releasing Factor in Depressive Illness: . . . , *Psychoneuroendocrinology*, 9, 147–160, 1984.
N. R. Swerdlow et al., Corticotropin–Releasing Factor Potentiates Acoustic Startle in Rats: Blockade by Chlordiazepoxide, *Psychopharmacology*, 88, 147–152, 1986.
Karen Thatcher Britton, et al, Chlordiazepoxide Attenuates Response Suppression Induced by Corticotropin–Releasing Factor in the Conflict Test, *Psychopharmacology*, 86, 170–174, 1985.
Mihaly Arato et al, Elevated CSF CRF in Suicide Victims, *Biol. Psychiatry*, 25, 355–359, 1989.
Charles B. Nemeroff et al., Reduced Corticotropin Releasing Factor Binding Sites in the Frontal Cortex of Suicide Victims, *Arch Gen Psychiatry*, 45, 577–579, Jun. 1988.
Karen Thatcher Britton et al, Corticotropin Releasing Factor and Amphetamine Exaggerate Partial Agonist Properties . . . , *Pyschopharmacology*, 94, 306–311, 1988.
Robert M. Sapolsky, Hypercortisolism Among Socially Subordinate Wild Baboons Originates at the CNS Level, *Arch Gen Psyciatry*, 46, 1047–1051, Nov. 1989.
Csaba M. Banki et al, CSF Corticotropin–Releasing Factor–Like Immunoreactivity in Depression and Schizophrenia, *American Journal of Psychiatry*, 144, 873–877, Jul. 1987.

(List continued on next page.)

*Primary Examiner*—Richard L. Raymond
*Assistant Examiner*—Hong Liu
*Attorney, Agent, or Firm*—Monte R. Browder; Kenneth B. Rubin

[57] ABSTRACT

The present invention describes novel thiazolo[4,5-d] pyrimidines of formula:

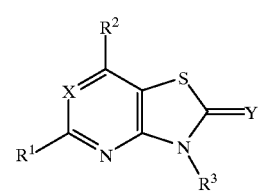

I wherein $R^3$ is a substituted aromatic or heteroaromatic group, or pharmaceutically acceptable salt forms thereof, which are useful as CRF antagonists.

5 Claims, No Drawings

OTHER PUBLICATIONS

Craig W. Berridge and Adrian J. Dunn, Corticotropin–Releasing Factor Elicits Naloxone Sensitive Stress–Like Alterations in Exploratory Behavior in Mice, *Regulatory Peptides,* 16, 83–93, 1986.

Wylie Vale, et al., Chemical and Biological Characterization of Corticotropin Releasing Factor, *Recent Progress in Hormone Research,* 39, 245–270, 1983.

D. R. Britton, et al., Intraventricular Corticotropin–Releasing Factor Enhances Behavioral Effects of Novelty, *Life Sciences,* 31, 363–367, 1982.

Wylie Vale, et al, Characterization of a 41–Reisdue Ovine Hypothalamic Peptide that Stimulates Secretion of Corticotropin and B–Endorphin, *Science,* 213, 1394–1397, Sep. 18, 1981.

Randal D. France, et al, CSF Corticotropin–Releasing Factor–Like Immunoactivity in Chronic Pain Patients with and without Major Depression, *Biol Psychiatry,* 23, 86–88, 1988.

Thomas E. Christos and Argyrios Arvanitis, Corticotrophin–releasing factor receptor antagonists, *Exp. Opin. Ther. Patents,* 8, 143–152, 1988.

Nirupama Tiwari et al., Synthesis and fungicidal activity of some 3,7–diaryl–6–cyanorhodanino[4,5–b]–pyridin–5 (4H)–ones and 3–aryl–rhodanino[4,5–b]furan–6 (5H)–ones, *Indian Journal of Chemistry,* 28B, 796–798, Sep. 1989.

Amrik Singh et al, Studies in a 4–Aminothiazolines: Part XVI–Synthesis of Thiazolo–[4,5–d]pyrimidines & related systems and reactions of functionalized primary amines with 5–cyano–4–ethoxymethyleneamino–4–thiazolines, *Indian Journal of Chemistry,* 19B, 37–41, 1980.

Amrik Singh et al, Synthesis of Thiazolo (4,5–d) Pyrimidines; A New Class of CNS Depressants. Studies in 4–Aminothiazolines—XIII, *J. Indian Chem. Soc.,* LV, 1040–1042, 1978.

Badawey et al. Potential anti–microbials. Synthesis and in vitro anti–microbial evaluation of some thiazolo[4,5–d]pyrimidines, Eur. J. Med. Chem, 28: 97–101, 1993.

THIAZOLO[4,5-D]PYRIMIDINES AND PYRIDINES AS CORTICOTROPIN RELEASING FACTOR (CRF) ANTAGONISTS

This application claims the benefit of the filing date of U.S. Provisional Application No. 60/080,537, filed Apr. 3, 1998.

FIELD OF THE INVENTION

This invention relates to novel thiazolo[4,5-d]pyrimidines and pyridines, pharmaceutical compositions containing the same and methods of using same in the treatment of psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provides evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

EP 0,778,277 (EP '277) describes a variety of CRF antagonists including those of the formula:

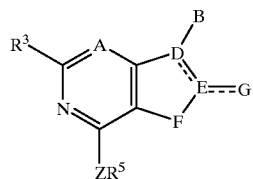

wherein A can be N or C, D can be N or C, E can be N or C, G can be O, S, or N, and F can be O, S, N, or C. EP '277 does not disclose any thiazolo[4,5-d]pyrimidines and pyridines. Furthermore, group B is not considered part of the presently claimed compounds.

In view of the above, efficacious and specific antagonists of CRF are needed as potentially valuable therapeutic agents for the treatment of psychiatric disorders and neurological diseases. It is thus desirable to discover new CRF antagonists.

SUMMARY OF THE INVENTION

Accordingly, one object of the present invention is to provide novel thiazolo[4,5-d]pyrimidines and pyridines which are useful as CRF antagonists or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt form thereof.

It is another object of the present invention to provide a method for treating psychiatric disorders and neurological diseases comprising administering to a host in need of such treatment a therapeutically effective amount of at least one of the compounds of the present invention or a pharmaceutically acceptable salt form thereof.

These and other objects, which will become apparent during the following detailed description, have been achieved by the inventors' discovery that compounds of formula I:

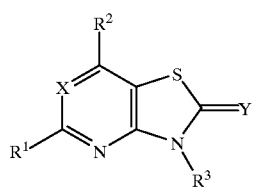

I or pharmaceutically acceptable salt forms thereof, wherein $R^1$, $R^2$, $R^3$, X and Y are defined below, are CRF antagonists.

DETAILED DESCRIPTION OF THE INVENTION

[1] Thus, in a first embodiment, the present invention provides a novel compound of the formula (I):

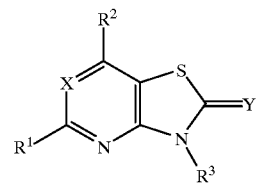

I or a pharmaceutically acceptable salt thereof, wherein:

X is $CR^4$ or N;

Y is selected from the group: S, O and $NR^5$;

$R^1$ is selected from the group: H, $C_{1-4}$ alkyl, $C_{2-4}$ alkenyl, $C_{2-4}$ alkynyl, Cl, F, Br, I, —CN, $C_{1-5}$ haloalkyl, —$NR^6R^7$, —$NR^6COR^7$, —$OR^8$, —SH, and —$S(O)_nR^9$;

n is independently at each occurrence selected from the group: 0, 1, and 2;

$R^2$ is selected from the group: $CR^{10}R^{11}R^{12}$, —$NR^{10a}R^{11a}$, —$NHCR^{10}R^{11}R^{12}$, —$OCR^{10}R^{11}R^{12}$, and phenyl, wherein the phenyl is substituted with 0–4 $R^a$;

$R^a$ is independently at each occurrence selected from the group: Cl, F, Br, I, $C_{1-4}$ haloalkyl, —$NO_2$, $C_{1-4}$ alkyl, $C_{2-5}$ alkenyl, $C_{2-4}$ alkynyl, $C_{3-7}$ cycloalkyl, $C_{2-5}$ carboalkoxy, SH, —$S(C_{1-4}$ alkyl), —CN, —OH, $C_{1-4}$ alkoxy, and —$NR^6R^7$, $OR^8$, $COR^7$;

$R^3$ is selected from the group: phenyl, pyridyl, pyrimidyl, napthyl, triazinyl, furanyl, quinolinyl, isoquinolinyl, thienyl, thiazolyl, pyrrolyl, oxazolyl, benzofuranyl, benzothienyl, benzothiazolyl, isoxazolyl, and pyrazolyl, and is substituted with 1 to 4 $R^b$ groups;

$R^b$ is independently at each occurrence selected from the group: $C_{1-6}$ alkyl, $C_{2-6}$ alkenyl, $C_{2-6}$ alkynyl, $C_{3-6}$ cycloalkyl, ($C_{3-8}$ cycloalkyl)$C_{1-4}$ alkyl-, $NO_2$, Cl, F, Br, I, —CN, $C_{1-6}$ haloalkyl, —$NR^{14}R^{15}$, —$NR^8COR^{14}$, —$NR^8CO_2R^{14}$, —$COR^{14}$, —$OR^{14}$, —$CONR^{14}R_{15}$, —$CO_2R^{14}$, —SH, and —$S(O)_nR^4$;

$R^4$ is selected from the group: H, $C_{1-4}$ alkyl, and $C_{1-4}$ haloalkyl, halogen, $NH_2$, $NH(C_{1-4}$ alkyl), $NH(C_{1-4}$ alkyl)$_2$, CN, $OR^8$;

$R^5$ is —$CO(C_{1-4}$ alkyl) or —$CO_2(C_{1-4}$ alkyl);

$R^6$ and $R^7$ independently at each occurrence selected from the group: H, $C_{1-4}$ alkyl, and $C_{3-6}$ cycloalkyl;

$R^8$ is independently at each occurrence selected from the group: H, $C_{1-4}$ alkyl, $C_{1-4}$ haloalkyl, and $C_{3-6}$ cycloalkyl;

$R^9$ is independently at each occurrence selected from the group: $C_{1-4}$ alkyl, $C_{1-4}$ haloalkyl, and aryl;

$R^{10}$ and $R^{11}$ are independently at each occurrence selected from the group: $C_{1-6}$ alkyl, $C_{2-6}$ alkenyl, $C_{2-6}$ alkynyl, $C_{3-8}$ cycloalkyl, ($C_{3-8}$ cycloalkyl)$C_{1-4}$ alkyl-, —$(CH_2)_n$aryl, —$(CH_2)_n$heteroaryl, ($C_{1-6}$ alkoxy)$C_{1-6}$ alkyl-, —$C_{0-6}$—CN, —$NH(C_{1-6}$ alkyl), —$N(C_{1-6}$ alkyl)$_2$, and (carbo-$C_{1-6}$ alkoxy) $C_{0-6}$ alkyl-, each $R^{10}$ and $R^{11}$ being optionally substituted with 0–3 $R^c$;

$R^c$ is independently at each occurrence selected from the group: F, =O, $C_{1-4}$ alkyl, $C_{1-4}$ haloalkyl, $C_{2-4}$ alkenyl, $C_{2-4}$ alkynyl, $C_{1-4}$ alkoxy, —CN, $S(O)_nC_{1-4}$ alkyl, $NH_2$, $NH(C_{1-4}$ alkyl), $N(C_{1-4}$ alkyl)$_2$, phenyl, pyridyl, and pyrimidyl;

$R^{12}$ is independently at each occurrence selected from the group: H, $C_{1-6}$ alkyl;

alternatively, $R^{10}$ and $R^{11}$ are taken together, along with the interconnected carbon, to form a 4–8 membered saturated or partially saturated carbocyclic ring substituted with 0–2 $R^e$ or a 4–8 membered saturated or partially saturated heterocyclic ring containing 1–2 heteroatoms selected from O. N, $NR^8$, and S and substituted with 0–2 $R^d$;

$R^d$ is independently at each occurrence selected from the group: =O, $C_{1-4}$ alkyl, $C_{1-4}$ haloalkyl, $C_{2-4}$ alkenyl, $C_{2-4}$ alkynyl, $C_{1-4}$ alkoxy, —CN, —S(O)$_n C_{1-4}$ alkyl, —NH$_2$, —NH($C_{1-4}$ alkyl), —N($C_{1-4}$ alkyl)$_2$, and phenyl;

$R^{10a}$ and $R^{11a}$ are independently at each occurrence selected from the group: $C_{1-6}$ alkyl, $C_{2-6}$ alkenyl, $C_{2-6}$ alkynyl, ($C_{3-8}$ cycloalkyl)$C_{1-4}$ alkyl-, —(CH$_2$)$_n$aryl, —(CH$_2$)$_n$hetero-aryl, ($C_{1-6}$ alkoxy) $C_{1-6}$ alkyl-, —$C_{1-6}$— CN, —NH($C_{1-6}$ alkyl), —N($C_{1-6}$ alkyl)$_2$, (carbo-$C_{1-6}$ alkoxy)$C_{1-6}$ alkyl-, S(O)$_n R^8$, C(O)$_{1-2} R_8$, and C(O)NR$^6$R$^7$ each $R^{10a}$ being substituted with 0–3 $R^e$;

aternatively, $R^{10a}$ and $R^{11a}$ are taken together, along with the interconnected nitrogen, to form a 4–8 membered saturated or partially saturated heterocyclic ring containing 0–1 additional heteroatoms selected from O, N, NR$^8$, and S and substituted with 0–3 $R^e$;

$R^{14}$ and $R^{15}$ are independently at each occurrence selected from the group: H, $C_1$–$C_4$ alkyl, $C_1$–$C_4$ haloalkyl, $C_3$–$C_6$ cycloalkyl, ($C_{3-8}$ cycloalkyl)$C_{1-4}$ alkyl-, aryl, —($C_1$–$C_4$ alkyl)aryl, heteroaryl and —($C_1$–$C_4$)heteroaryl;

aryl is phenyl substituted with 0–3 $R^e$;

$R^e$ is independently selected at each occurrence from the group: $C_{1-4}$ alkyl, $C_{2-4}$ alkenyl, $C_{2-5}$ alkynyl, $C_{3-6}$ cycloalkyl, —NO$_2$, Cl, F, Br, I, —CN, $C_{1-4}$ haloalkyl, —NH$_2$, —NH($C_{1-4}$ alkyl), —N($C_{1-4}$ alkyl)$_2$, OR$^{14}$, S(O)$_n R^{14}$; and, heteroaryl is independently at each occurrence selected from the group: pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl and pyrazolyl substituted with 0–3 $R^f$.

[2] In a preferred embodiment, the present invention provides novel compounds, wherein:

Y is S or O;

$R^1$ is selected from the group: H, $C_{1-4}$ alkyl, $C_{2-4}$ alkenyl, $C_{2-4}$ alkynyl, Cl, F, —CN, $C_{1-5}$ haloalkyl, and —NR$^6$R$^7$;

$R^5$ is selected from the group: phenyl, pyridyl, and pyrimidyl, and is substituted with 1 to 4 $R^b$ groups;

$R^b$ is independently at each occurrence selected from the group: $C_{1-10}$ alkyl, $C_{2-10}$ alkenyl, $C_{2-10}$ alkynyl, $C_{3-6}$ cycloalkyl, ($C_{3-8}$ cycloalkyl)$C_{1-4}$ alkyl-, NO$_2$, Cl, F, —CN, $C_{1-4}$ haloalkyl, —NR$^{14}$R$^{15}$, —NR$^8$COR$^{14}$, —NR$^8$CO$_2$R$^{14}$, —COR$^{14}$, —OR$^{14}$, —CONR$^{14}$R$^{15}$, —CO$_2$R$^{14}$, —SH, and —S(O)$_n$R$^{14}$;

heteroaryl is independently at each occurrence selected from the group: pyridyl, pyrimidinyl, triazinyl, furanyl, thienyl, imidazolyl, indolyl, pyrrolyl, oxazolyl, benzofuranyl, isoxazolyl and pyrazolyl substituted with 0–3 $R^e$.

[3] In a more preferred embodiment, the present invention provides a compound selected from the group:

3-(2-Bromo-4-isopropyl)phenyl-5-methyl-7-morpholinothiazolo[4,5-d]pyrimidin-2-thione;

3-(2-Bromo-4-isopropyl)phenyl-7-(N-cyclopropylmethyl-N-propyl)amino-5-methylthiazolo[4,5-d]pyrimidin-2-thione;

3-(2-Bromo-4-isopropyl)phenyl-7-(N,N-diethylamino)-5-methyl-thiazolo[4,5-d]pyrimidin-2-thione;

7-(N,N-bismethoxyethylamino)-3-(2-bromo-4-isopropyl)phenyl-5-methylthiazolo[4,5-d]pyrimidin-2-thione;

3-(2-Bromo-4-isopropyl)phenyl-7-(N-butyl-N-ethyl)amino-5-methylthiazolo[4,5-d]pyrimidin-2-thione;

3-(2-Bromo-4-isopropyl)phenyl-7-(N,N-di-sec-butylamine)-5-methylthiazolo[4,5-d]pyrimidin-2-thione;

7-(N,N-diethylamino)-5-methyl-3-(2,4,6-trimethyl)phenylthiazolo[4,5-d]pyrimidin-2-thione;

7-(N,N-bismethoxyethylamino) -5-methyl-3-(2,4,6-trimethyl)phenylthiazolo[4,5-d]pyrimidin-2-thione;

7-(N-cyclopropylmethyl-N-propyl)-5-methyl-3-(2,4,6-trimethyl)phenylthiazole[4,5-d]pyrimidin-2-thione;

3-(2-Bromo-4-isopropyl)phenyl-7-(N-cyclopropylmethyl-N-propyl)amino-5-methylthiazolo[4,5-d]pyrimidin-2-one;

7-(N,N-bismethoxyethylamino)-3-(2-bromo-4-isopropyl)phenyl-5-methylthiazolo[4,5-d]pyrimidin-2-one;

3-(2-Bromo-4-isopropyl)phenyl-7-(N,N-diethylamino)-5-methylthiazolo[4,5-d]pyrimidin-2-one;

7-(N,N-diethylamino)-5-methyl-3-(2,4,6-trimethyl)phenylthiazolo([4,5-d]pyrimidin-2-one;

7-(N,N-bismethoxyethylamino)-5-methyl-3-(2,4,6-trimethyl)phenylthiazolo[4,5-d]pyrimidin-2-one; and, 7-(N-cyclopropylmethyl-N-propyl)amino-5-methyl-3-(2,4,6-trimethyl)phenylthiazolo[4,5-d]pyrimidin-2-one;

or a pharmaceutically acceptable salt form thereof.

In another embodiment, the present invention provides pharmaceutical compositions comprising a pharmaceutically acceptable carrier and a therapeutically effective amount of at least one of the compounds of the present invention or a pharmaceutically acceptable salt form thereof.

In another embodiment, the present invention provides a method of treating psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in a mammal, comprising: administering to the mammal a therapeutically effective amount of a compound of formula (I) or a pharmaceutically acceptable salt form thereof.

In another embodiment, the present invention provides intermediate compounds useful in preparation of the CRF antagonist compounds and processes for making those intermediates, as described in the following description and claims.

The CRF antagonist compounds provided by this invention (and especially labelled compounds of this invention) are also useful as standards and reagents in determining the ability of a potential pharmaceutical to bind to the CRF receptor.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^8$) occurs more than one time in any constituent or formula for a compound, its definition at each occurrence is independent of its definition at every other occurrence. Thus, for example, if a group is shown to be substituted with 0–2 $R^8$, then said group may optionally be substituted with up to two $R^8$ groups and $R^8$ at each occurrence is selected independently from the definition of $R^8$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Alkenyl" is intended to include hydrocarbon chains of either a straight or branched configuration and one or more unsaturated carbon-carbon bonds which may occur in any stable point along the chain, such as ethenyl, propenyl and the like. "Alkynyl" is intended to include hydrocarbon chains of either a straight or branched configuration and one or more triple carbon-carbon bonds which may occur in any stable point along the chain, such as ethynyl, propynyl and the like. "Halo" or "halogen" as used herein refers to fluoro, chloro, bromo, and iodo; and "counter-ion" is used to represent a small, negatively charged species such as chloride, bromide, hydroxide, acetate, sulfate, and the like.

As used herein, "carbocycle" or "carbocyclic residue" is intended to mean any stable 3- to 8-membered monocyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7- membered monocyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7- membered monocyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

9

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

The term "therapeutically effective amount" of a compound of this invention means an amount effective to antagonize abnormal level of CRF or treat the symptoms of affective disorder, anxiety or depression in a host.

10
SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

The novel substituted bicyclic thiazolo[4,5]pyrimidines and pyridines of formula (I) of this invention can be prepared by one of the general schemes outlined below (Schemes 1–2).

Compounds of the formula (I), wherein X is N and $R^3$=phenyl, pyridyl or pyrimidyl can be prepared as shown in Scheme 1. Treatment of anilines, aminopyridines or aminopyrimidines with thiophosgene readily generates the corresponding isothiocyanates (II). Cyclization with elemental sulfur, triethylamine, and cyanoacetamide via the methodology of Gewald (*J. Prakt. Chem.* 1966, 32, 26–30) affords the thiazolothiones (III). These derivatives can be treated with reagents such as refluxing acetic acid or a trialkylorthoformate or acetate, or any appropriately $R^1$ substituted carboxylic acid to form the thiazolo[4,5]-pyrimidone thiones (IV). Treatment of the pyrimidone group in (IV) with reagents such as phosphorous oxychloride, phosphorous oxybromide, methanesulfonyl chloride, p-toluenesulfonyl chloride, or trifluormethanesulfonic anhydride can provide compounds of formula (V), wherein the LG is a leaving group and is, respectively, chloro, bromo, methansulfonate, p-toluenesulfonate, or triflate.

The resulting leaving group can then be replaced with a nucleophile such as an amine, an alcohol, or an organolithium, organomagnesium, organosodium, organopotassium, an alkyl cuprate or in general, an organometallic reagent to the corresponding compound (V). Conditions which may facilitate this transformation include the optional presence of bases such as sodium hydride, triethylamine, diisopropylethylamine, or potassium carbonate, or a metallic bis(trimethyl-silyl)amide wherein the metal can be sodium, lithium, or potassium.

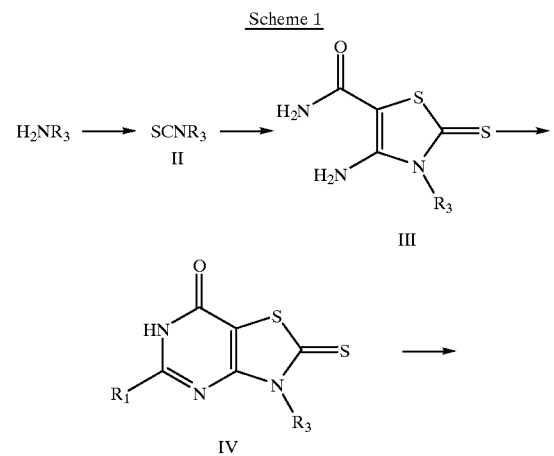

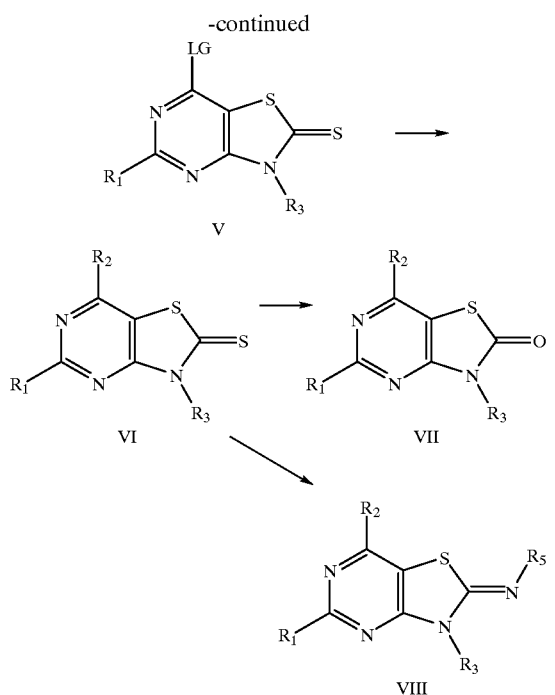

These reactions may be conducted neat, or in the optional presence of solvents such as but not limited to tetrahydrofuran, dimethylformamide, dimethylsulfoxide, ethylene glycol, methylene chloride, acetonitrile, or ethanol at room temperature or at elevated temperature up to the boiling point of the solvent employed. One skilled in the art of organic synthesis will readily understand the optimal combinations of these conditions to prepare a number of compounds of Formula (VI) with $R_2$ variations, and can refer to the review of Brown, D. J. (*Comprehensive Heterocyclic Chemistry*, Katritsky, A. R., et al., Eds., Pergamon Press, Oxford, 1984, 3, 57–156).

Optionally, where $R_2$ is an aryl or substituted aryl, the precursor aryl boronic acid ($R_2$—$B(OH)_2$) may be coupled to halo-intermediate of formula (V) using catalytic amounts of tetrakis(triphenylphosphine)palladium, as taught by Suzuki, et al. (*Synthetic Communications*, 1981, 11, 513–519).

Additionally, carbon substituents represented by $R_2$ may be introduced into compound of formula (V) by treatment with a sodium salt (generated by the use of a base such as sodium ethoxide, sodium hydride or sodium bis(trimethylsilyl)amide) of an active methylene or methine reagent (i.e. where the substituents are groups which stabilize adjacent anions, such as keto, carboalkoxy, cyano, alkyl- or aryl-sulfonyl, etc.). The resulting compounds of formula (VI) may be further modified by conversion of the stabilizing groups into substituents defined in the scope of formula (I). Those skilled in the art of organic synthesis should readily understand the possible variations of these conversions in preparing a number of compounds of formula (VI), and can consult the text of Larock, R. C. (*Comprehensive Organic Transformations*, VCH Publishers, New York, 1989).

Thiones of compound (VI) can be replaced with oxygen by activation with a strong methylating reagent such as dimethyl sulfate and subsequent water hydrolysis to afford the thiazolones (VII). This chemistry can be carried out at ambient temperature, or more commonly, at or above 100° C. Alternatively, the thione of compound (VI) can again be activated with a strong methylating reagent such as dimethyl sulfate and treated with amines as described by Gewald (*Monatshefte fur Chemie*, 1981, 112, 1393–1404) providing thiazoloimines (VIII).

Compounds of the formula (I), wherein X is C—$R^4$ and $R^3$ is phenyl, pyridyl or pyrimidyl can be prepared as shown in Scheme 2. Preparation of thiazolothiones (IX) is accomplished utilizing the same methodology described in Scheme 1 for the preparation of compounds of formula (III), with the replacement of a lower alkyl (typically $C_1$–$C_4$) cyanoacetate for cyanoacetamide. Preparation of compounds of formula (X, $R^4$=CN) readily occurs with the treatment of thiazolothiones (IX) with another equivalent of an active methylene reagent as depicted in the Scheme. This methodology is amply illustrated in the work of Mohareb, R. M. et al. (*J. Chem. Research*, 1994, 126–127).

Removal of the cyano group of (X, $R^4$) can be accomplished with either acid (for example, but not limited to, hydrochloric, sulphuric, or acetic acid) or base (for example, but not limited to, sodium hydroxide) in the presence of elevated temperature to afford the hydroxypyridine (XI, $R^4$=H), and one skilled in the art of organic synthesis will readily understand the optimal conditions for effecting this transformation, or can consult the classic text of Vogel, A. I. (*A Textbook of Practical Organic Chemistry*, Longman Group Limited, London, 1956, 805).

Compound of formula (XII) can then be prepared by the route described in Scheme 1 for the preparation of compound of formula (V). Furthermore, compound of formula (XIII) can be prepared by the route described in Scheme 1 for the preparation of compound of formula (VI) where $R_2$ is incorporated into the core structure. Additionally, utilizing the chemistry and references detailed in Scheme 1 for the preparation of compounds of formula (VII) and (VIII), so to can compounds of formula (XIV) and (XV) be prepared.

Other features of the invention will become apparent in the course of the following descriptions of exemplary embodiments which are given for illustration of the invention and are not intended to be limiting thereof.

EXAMPLE 1

3-(2-Bromo-4-isopropyl)phenyl-5-methyl-7-morpholino-thiazolo[4,5-]pyrimidin-2-thione:

Part A: 2-Bromo-4-isopropylaniline (5.0 g, 23.4 mmol) was added to sodium carbonate (7.4 g, 70.2 mmol) in anhydrous dimethylformamide (125 ml) at 0° C. Addition of thiophosgene (2.7 ml, 35.1 mmol) via syringe discharged the initial red color. The reaction was stirred 20 minutes at 0° C., poured onto 600 ml water, and extracted with ethyl acetate (4×100 ml). The combined organic extracts were dried over anhydrous magnesium sulfate, filtered, and concentrated in-vacuo. The crude oil was chromatographed on silica gel (300 g; hexanes) affording the desired product as a pale yellow oil, 5.2 g (87%). FT-IR (neat): 2060 (s) cm$^{-1}$, (—N=C=S).

Part B: To anhydrous dimethylformamide (20 ml) was added triethylamine (2.45 ml, 17.6 mmol) and cyanoacetamide (1.7 g, 20.7 mmol) followed by stirring at room temperature for 10 minutes. Addition of elemental sulfur (655 mg, 20.4 mmol) induced a strong red/brown color. The reaction was stirred 45 minutes, charged with the isothiocyanate produced in Part A (5.2 g, 20.4 mmol), and stirred an additional 2.5 hours at room temperature. The reaction was poured into water (600 ml), and saturated sodium chloride solution (100 ml) and extracted with ethyl acetate (4×100 ml). The combined organic extracts were washed with water (2×100 ml), saturated sodium chloride solution (1×100 ml), dried over anhydrous magnesium sulfate, filtered, and concentrated in-vacuo. Chromatography on silica gel (600 g; 2/1 ethyl acetate/hexanes) gave 5.9 g (78%) of desired product; mp 205° C. Anal. Calcd. for $C_{13}H_{14}N_3O_1S_2Br_1$: C, 41.94; H, 3.79; N, 11.29. Found: C, 41.88; H, 3.64; N, 11.01.

Part C: To the thiazolothione produced in Part B (5.9 g, 16.0 mmol) was added distilled acetic anhydride (35 ml). The reaction was refluxed 3 hours, stored overnight in a freezer, then diluted with water (300 ml) and extracted with ethyl acetate (4×70 ml). The combined organic extracts were washed with water (5×70 ml), and brine (1×50 ml), and dried over anhydrous magnesium sulfate, filtered and concentrated in-vacuo. The crude solid obtained was used without further purification in Part D.

Part D: The pyrimidone from Part C (15.97 mmol) was treated with phosphorous oxychloride (50 ml) and brought to reflux for 2 hours. The reaction was subsequently poured very cautiously onto 1.4 liters ice/water and allowed to stir overnight. The resultant solid was filtered and dried to constant weight affording 5.7 g (85%). Recrystallization from hexanes gave crystals, mp 143.5–145° C. Anal. Calcd. for $C_{15}H_{14}N_3S_2Cl_1Br_1$: C, 43.33; H, 3.39; N, 10.11. Found: C, 43.44; H, 3.01; N, 9.93.

Part E: The product from Example 1, Part D (250 mg, 0.6 mmol) was dissolved in anhydrous acetone (6 ml), treated with morpholine (106 µl, 1.2 mmol), and the reaction refluxed 2 hours. Concentration under a stream of nitrogen gave a yellow powder. The solid was taken up in water (100 ml) and extracted with methylene chloride (3×50 ml). The combined organic extracts were washed with saturated sodium chloride solution (1×30 ml), dried over anhydrous magnesium sulfate, filtered and concentrated in-vacuo to give a beige solid. Recrystallization from ethyl acetate gave opaque crystals, 125 mg (45%), mp 220–221.5° C. Anal. Calcd. for $C_{19}H_{21}N_4S_2Br_1O_1$: C, 49.03; H, 4.55; N, 12.04. Found: C, 49.09; H, 4.42; N, 12.03.

EXAMPLE 2

3-(2-Bromo-4-isopropyl)phenyl-7-(N-cyclopropylmethyl-N-propyl)amino-5-methylthiazolo[4,5-d]pyrimidin-2-thione:

The product from Example 1, Part D (2.25.g, 5.41 mmol) and N-cyclopropylmethyl-N-propylamine (1.55 ml, 10.82 mmol) were coupled using the same method described in Example 2 to provide the desired product, 2.38 g (97%), as an off white solid. Recrystallization from diethyl ether gave crystals, mp 117–122° C. Anal. Calcd. for $C_{22}H_{27}N_4S_2Br_1$: C, 53.76; H, 5.54; N, 11.40. Found: C, 53.76; H, 5.46; N, 11.25.

EXAMPLE 3

3-(2-Bromo-4-isopropyl)phenyl-7-(N,N-diethylamino)-5-methyl-thiazolo[4,5-d]pyrimidin-2-thione:

The product from Example 1, Part D (2.74 g, 6.59 mmol) and diethylamine (1.36 ml, 13.2 mmol) were coupled using the same method described in Example 2. Chromatography of the crude solid on silica gel (600 g; 1/9 ethyl acetate/hexanes) gave 2.31 g (78%) of an off white solid. Recrystallization from diethyl ether gave crystals, mp 138–140° C. Anal. Calcd. for $C_{19}H_{23}N_4S_2Br_1$: C, 50.55; H, 5.15; N, 12.41. Found: C, 50.39; H, 5.15; N, 12.22.

EXAMPLE 4

7-(N,N-bismethoxyethylamino)-3-(2-bromo-4-isopropyl)phenyl-5-methylthiazolo[4,5-d]pyrimidin-2-thione:

The product from Example 1, Part D (275 mg, 0.66 mmol) and bis(methoxyethyl)amine (195 µl, 1.32 mmol) were coupled using the same method described in Example 2. Chromatography of the crude material on silica gel (50 g; 1/2 ethyl acetate/hexanes) gave the product; 338 mg (100%). Recrystallization from diethyl ether gave crystals, mp 121–123° C. Anal. Calcd. for $C_{21}H_{27}N_4O_2S_2Br_1$: C, 49.31; H, 5.32; N, 10.95. Found: C, 49.42; H, 5.20; N, 10.68.

EXAMPLE 5

3-(2-Bromo-4-isopropyl)phenyl-7-(N-butyl-N-ethyl)amino-5-methylthiazolo[4,5-d]pyrimidin-2-thione:

The product from Example 1, Part D (300 mg, 0.72 mmol) and N-butyl-N-ethylamine (197 µl, 1.44 mmol) were coupled using the same method described in Example 2. Chromatography on silica gel (50 g, 1/9 ethyl acetate/hexanes) gave 331 mg (96%) of the product as an oil.

Crystallization was achieved from diethyl ether/hexanes, mp 98–101.5° C. Anal. Calcd. for $C_{21}H_{27}N_4S_2Br_1$: C, 52.60; H, 5.68; N, 11.68. Found: C, 52.81; H, 5.70; N. 11.62.

EXAMPLE 6
3-(2-Bromo-4-isopropyl)phenyl-7-(N,N-di-sec-butylamine)-5-methylthiazolo[4,5-d]pyrimidin-2-thione:

The product from Example 1, Part D (300 mg, 0.72 mmol) and di-secbutylamine (252 μl, 1.44 imol) were coupled using the same method described in Example 2. Chromatography on silica gel (50 g, 1/9 ethyl acetate/hexanes) gave the product as a crystalline solid, 343 mg (94%), mp 181–182.5° C. Anal. Calcd. for $C_{23}H_{31}N_4S_2Br_1$: C, 54.43; H, 6.16; N, 11.04. Found: C, 54.43; H, 6.00; N, 10.85.

EXAMPLE 7
7-(N,N-diethylamino)-5-methyl-3-(2,4,6-trimethyl)phenyl thiazolo[4,5-]pyrimidin-2-thione:

Part A: 2,4,6-Trimethylaniline (5.0 g, 37 mmol) was treated with sodium carbonate (11.8 g, 111.1 mmol) and thiophosgene (4.23 ml, 55.5 mmol) as described in Example 1, Part A. The crude oil was chromatographed on silica gel (350 g; hexanes) affording the desired product, 6.0 g (92%). FT-IR (neat): 2152 (s) $cm^{-1}$, (—N=C=S).

Part B: The isothiocyanate formed in Part A (5.5 g, 31.2 mmol) was treated with cyanoacetamide (2.6 g, 31.2 mmol), triethylamine (3.76 ml, 27 mmol) and elemental sulfur (1.0 g, 31.2 mmol) in dimethyl-formamide (32 ml) as described in Example 1, Part B. The crude yellow/green solid was chromatographed in two portions. A 4 g portion was chromatographed on silica gel (300 g; 2/1 ethyl acetate/hexanes) and a c. 3 g portion was chromatographed on silica gel (300 g; 2/1 ethyl acetate/ hexanes), to afford a combined 6.1 g (67%) desired product, mp 205–206° C. Anal. Calcd. for $C_{13}H_{15}N_3S_2O_1$: C, 53.22; H, 5.15. Found: C, 53.08; H, 5.17.

Part C: The thiazolothione produced in Part B (6.1 g, 21.7 mmol) was treated with acetic anhydride (61 ml) and refluxed for 3 hours. The reaction was cooled in an ice bath, the resulting precipitate filtered and dried to constant weight affording 3.3 g (48%) as a yellow solid.

Part D: The pyrimidone from Part C (3.5 g, 11.1 mmol) was treated with phosphorous oxychloride (35 ml) and refluxed for 2.5 hours. The reaction was cooled and transferred cautiously onto 1 liter of ice/water, and stirred overnight. The resultant precipitate was filtered and dried to constant weight giving 3.3 g (89%), mp 162.5–163.5° C. Anal. Calcd. for $C_{15}H_{14}N_3S_2Cl_1$: C, 53.64; H, 4.20; N, 12.51. Found: C, 53.19; H, 4.17; N, 12.33.

Part E: The product from Example 8, Part D (1.13 g, 3.35 mmol) and diethylamine (693 μl, 6.7 mmol) were coupled using the same method described in Example 2. Chromatography on silica gel (200 g; 1/9 ethyl acetate/hexanes) gave the product, 1.20 g (96%) as an amorphous solid. Crystals were afforded from dissolution and standing in hexanes, mp 129.5–131.5° C. Anal. Calcd. for $C_{19}H_{24}N_4S_2$: C, 61.25; H, 6.49; N, 15.04. Found: C, 61.26; H, 6.47; N, 15.11.

EXAMPLE 8
7-(N,N-bismethoxyethylamino)-5-methyl-3-(2,4,6-trimethyl) phenylthiazolo[4,5-]pyrimidin-2-thione:

The product from Example 8, Part D (1.05 g, 3.13 mmol) and bis(methoxyethyl)amine (925 μl, 6.26 mmol) were coupled using the same method described in Example 2. Chromatography on silica gel (200 g; 2/8 ethyl acetate/hexanes) gave the product as a viscous oil, 1.33 g (99%). Anal. Calcd. for $C_{21}H_{28}N_4O_2S_2$: C, 58.31; H, 6.52; N, 12.95. Found: C, 58.47; H, 6.44; N, 12.86.

EXAMPLE 9
7-(N-cyclopropylmethyl-N-propyl)-5-methyl-3-(2,4,6-trimethyl)phenylthiazole[4,5-]pyrimidin-2-thione:

The product from Example 8, Part D (1.1 g, 3.28 mmol) and N-cyclopropylmethyl-N-propylamine (944 ml, 6.6 mmol) were coupled using the same method described in Example 2. Chromatography on silica gel (200 g; 2/8 ethyl acetate/hexanes) gave the product as an amorphous solid. Anal. Calcd. for $C_{22}H_{28}N_4S_2$: C, 64.04; H, 6.84; 13.58. Found: C, 64.31; H, 6.91; N, 13.45.

EXAMPLE 10
3-(2-Bromo-4-isopropyl)phenyl-7-(N-cyclopropylmethyl-N-propyl)amino-5-methylthiazolo[4,5-d]pyrimidin-2-one:

The product from Example 3 (300 mg, 0.61 mmol) was treated with dimethyl sulfate (113 μl, 1.22 mmol) and heated in an oil bath at 130° C. for 1 hour. To the reaction was added water (3 ml) followed by refluxing 2 hours. The cooled reaction was diluted with water (10 ml) and extracted with ethyl acetate (3×10 ml). The combined organic extracts were dried over anhydrous magnesium sulfate, filtered and concentrated in-vacuo. The resultant oil was chromatographed on silica gel (150 g; 2/8 ethyl acetate/ hexanes) to give 183 mg (62%) of the desired product as an amorphous solid. The product was crystallized and recrystallized from hexanes providing colorless opaque crystals, mp 113–115° C. Anal. Calcd. for $C_{22}H_{27}N_4S_1O_1Br_1$: C, 55.58; H, 5.72; N, 11.78. Found: C, 55.53; H, 5.83; N, 11.47.

EXAMPLE 11
7-(N,N-bismethoxyethylamino)-3-(2-bromo-4-isopropyl) phenyl-5-methylthiazolo[4,5-d]pyrimidin-2-one:

The product from Example 5 (250 mg, 0.49 mmol) was treated with dimethyl sulfate (93 μl, 1.0 mmol) under the same conditions described in Example 12. The crude oil was chromatographed on silica gel (25 mg; 1/2 ethyl acetate/hexanes) to afford the desired product, 16 mg (6%) as a viscous oil. CI-HRMS calcd. for $C_{21}H_{28}N_4O_3S_1Br_1$ (M+H): 495.1065. Found: 495.1077.

EXAMPLE 12
3-(2-Bromo-4-isopropyl)phenyl-7-(N,N-diethylamino)-5-methylthiazolo[4,5-]pyrimidin-2-one:

The product from Example 4 (490 mg, 1.1 mmol) was treated with dimethyl sulfate (202 μl, 2.18 mmol) under the same conditions described in Example 12. The crude oil was chromatographed on silica gel (30 g; 1/9 ethyl acetate/hexanes) to afford 235 mg (50%) of the desired product as an amorphous solid. Anal. Calcd. for $C_{19}H_{23}N_4S_1O_1Br_1$: C, 52.41; H, 5.32; N, 12.87. Found: C, 52.69; H, 5.46; N, 12.62.

EXAMPLE 13
7-(N,N-diethylamino)-5-methyl-3-(2,4,6-trimethyl)phenyl thiazolo[4,5-d]pyrimidin-2-one:

The product from Example 9 (600 mg, 1.61 mmol) was trreated with dimethyl sulfate (300 μl, 3.22 mmol) under the same conditions described in Example 12. The crude oil was chromatographed on silica gel (30 g; 1/9 ethyl acetate/hexanes) to give the product, 255 mg (44%) as an amorphous solid. Anal. Calcd. for $C_{19}H_{24}N_4O_1S_1$: C, 64.02; H. 6.79; N, 15.72. Found: C, 64.24; H, 6.67; N, 15.63.

EXAMPLE 14
7-(N,N-bismethoxyethylamino)-5-methyl-3-(2,4,6-trimethyl) phenylthiazolo[4,5-d]pyrimidin-2-one:

The product from Example 10 (663 mg, 1.53 mmol) was treated with dimethyl sulfate (284 μl, 3.06 mmol) under the same conditions described in Example 12. The crude oil was chromatographed on silica gel (35 g; 1/2 ethyl acetate/hexanes) to give the product, 67 mg (11%), as a viscous oil. CI-HRMS calcd. for $C_{21}H_{28}N_4O_2S_2$ (M+H): 417.1960. Found: 417.1947.

EXAMPLE 15

7-(N-cyclopropylmethyl-N-propyl)amino-5-methyl-3-(2,4,6-trimethyl)phenylthiazolo[4,5-d]pyrimidin-2-one:

The product from Example 11 (600 mg; 1.45 mmol) was treated with dimethyl sulfate (270 µl; 2.91 mmol) under the same conditions described in Example 12. The crude oil was chromatographed on silica gel (70 g; 2/8 ethyl acetate/hexanes) to give the product, 124 mg (22%) as a crystalline solid, mp 93–94° C. Anal. Calcd. for $C_{22}H_{28}N_4O_1S_1$: C, 66.64; H, 7.12; N, 14.13. Found: C, 66.79; H, 7.08; N, 13.93.

TABLE 1

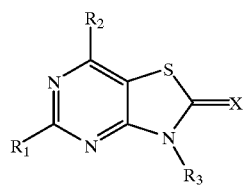

Key for $R^3$ in the following Table:
A: 2-bromo-4-isopropylphenyl
C: 2,4,6-trimethylphenyl

| Ex. | X | $R_1$ | $R_2$ | $R_3$ | Mp, ° C. |
|---|---|---|---|---|---|
| 1 | S | Me | morpholino | A | 220–221.5 |
| 2 | S | Me | N(Pr)CH$_2$cycloPr | A | 117–122 |
| 3 | S | Me | NEt$_2$ | A | 138–140 |
| 4 | S | Me | N(CH$_2$CH$_2$OMe)$_2$ | A | 125–125.5 |
| 5 | S | Me | NBuEt | A | 98–101.5 |
| 6 | S | Me | N(di-secbutyl)$_2$ | A | 181–182.5 |
| 7 | S | Me | NEt$_2$ | C | 129.5–131 |
| 8 | S | Me | N(CH$_2$CH$_2$OMe)$_2$ | C | Oil; C, H, N |
| 9 | S | Me | N(Pr)CH$_2$cycloPr | C | Amor.; C, H, N |
| 10 | O | Me | N(Pr)CH$_2$cycloPr | A | 113–115 |
| 11 | O | Me | N(CH$_2$CH$_2$OMe)$_2$ | A | Oil; HRMS |
| 12 | O | Me | NEt$_2$ | A | Amor.; C, H, N |
| 13 | O | Me | NEt$_2$ | C | Oil; C, H, N |
| 14 | O | Me | N(CH$_2$CH$_2$OMe)$_2$ | C | Oil; HRMS |
| 15 | O | Me | N(Pr)CH$_2$cycloPr | C | 93–94 |

The following table contains representative examples of the present invention. Each entry in the table is intended to be paired with each formulae at the start of the table. For example, example 1 in Table 2 is intended to be paired with each of formulae a–x.

TABLE 2

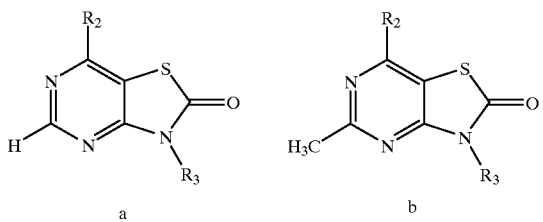

Key for $R^3$ in the following Tables:
A: 2-bromo-4-isopropylphenyl
B: 2-chloro-4,6-dimethoxyphenyl
C: 2,4,6-trimethylphenyl
D: 2-bromo-4,6-dimethoxyphenyl
E: 2,4,6-trichlorophenyl
F: 4-bromo-2,6-dichlorophenyl
G: 2,4,6-trimethoxyphenyl
H: 2,6-dichloro-4-trifluoromethylphenyl
I: 2,4-dibromo-6-methoxyphenyl
J: 2-bromo-4-isopropyl-6-methoxyphenyl
K: 2,4-dimethoxy-3-pyridyl
L: 4-dimethylamino-2-trifluoromethylphenyl

| Ex. | $R_2$ | $R_3$ |
|---|---|---|
| 1 | CH(CH$_2$CH$_3$)$_2$ | A |
| 2 | OCH(CH$_2$CH$_3$)$_2$ | A |
| 3 | N(CH$_2$CH$_3$)$_2$ | A |
| 4 | N(H)CH$_2$CH$_2$CH$_3$ | A |
| 5 | N(CH$_2$CH$_2$OCH$_3$)(CH$_2$CH$_3$) | A |

TABLE 2-continued

| | | |
|---|---|---|
| 6 | $N(CH_2CH_3)CH_2CH_2CH_2CH_3$ | A |
| 7 | $NHCH(CH_2CH_3)CH_2SO_2Me$ | A |
| 8 | $N(CH_2CH_2OMe)_2$ | A |
| 9 | $N(Pr)CH_2cycloPr$ | A |
| 10 | $N(CH_2CH_3)CH_2SO_2Me$ | A |
| 11 | $CH(CO_2CH_2CH_3)_2$ | A |
| 12 | $CH(CH_2OCH_3)_2$ | A |
| 13 | 4-methoxyphenyl | A |
| 14 | morpholino | A |
| 15 | thiomorpholino | A |
| 16 | phenyl | A |
| 17 | 2-$NO_2$phenyl | A |
| 18 | 2-$CF_3$phenyl | A |
| 19 | 4-pyridyl | A |
| 20 | cyclopentyl | A |
| 21 | cyclohexyl | A |
| 22 | NH(cyclopentyl) | A |
| 23 | $N(Et)CH_2cycloPr$ | A |
| 24 | $NHCH(CH_3)CH_2CH_3$ | A |
| 25 | $NCH(CH_2CH_3)_2$ | A |
| 26 | $N(CH_2CH_2CH_3)_2$ | A |
| 27 | $N(CH_2CH_2OMe)CH_2CH_2CH_2OMe$ | A |
| 28 | $CH(CH_2CH_3)_2$ | B |
| 29 | $OCH(CH_2CH_3)_2$ | B |
| 30 | $N(CH_2CH_3)_2$ | B |
| 31 | $N(H)CH_2CH_2CH_3$ | B |
| 32 | $N(CH_2CH_2OCH_3)(CH_2CH_2CH_3)$ | B |
| 33 | $N(CH_2CH_3)CH_2CH_2CH_2CH_3$ | B |
| 34 | $NHCH(CH_2CH_3)CH_2SO_2Me$ | B |
| 35 | $N(CH_2CH_2OMe)_2$ | B |
| 36 | $N(Pr)CH_2cycloPr$ | B |
| 37 | $N(CH_2CH_3)CH_2SO_2Me$ | B |
| 38 | $CH(CO_2CH_2CH_3)_2$ | B |
| 39 | $CH(CH_2OCH_3)_2$ | B |
| 40 | 4-methoxyphenyl | B |
| 41 | morpholino | B |
| 42 | thiomorpholino | B |
| 43 | phenyl | B |
| 44 | 2-$NO_2$phenyl | B |
| 45 | 2-$CF_3$phenyl | B |
| 46 | 4-pyridyl | B |
| 47 | cyclopentyl | B |
| 48 | cyclohexyl | B |
| 49 | NH(cyclopentyl) | B |
| 50 | $N(Et)CH_2cycloPr$ | B |
| 51 | $NHCH(CH_3)CH_2CH_3$ | B |
| 52 | $NCH(CH_2CH_3)_2$ | B |
| 53 | $N(CH_2CH_2CH_3)_2$ | B |
| 54 | $N(CH_2CH_2OMe)CH_2CH_2CH_2OMe$ | B |
| 55 | $CH(CH_2CH_3)_2$ | C |
| 56 | $OCH(CH_2CH_3)_2$ | C |
| 57 | $N(CH_2CH_3)_2$ | C |
| 58 | $N(H)CH_2CH_2CH_3$ | C |
| 59 | $N(CH_2CH_2OCH_3)(CH_2CH_2CH_3)$ | C |
| 60 | $N(CH_2CH_3)CH_2CH_2CH_2CH_3$ | C |
| 61 | $NHCH(CH_2CH_3)CH_2SO_2Me$ | C |
| 62 | $N(CH_2CH_2OMe)_2$ | C |
| 63 | $N(Pr)CH_2cycloPr$ | C |
| 64 | $N(CH_2CH_3)CH_2SO_2Me$ | C |
| 65 | $CH(CO_2CH_2CH_3)_2$ | C |
| 66 | $CH(CH_2OCH_3)_2$ | C |
| 67 | 4-methoxyphenyl | C |
| 68 | morpholino | C |
| 69 | thiomorpholino | C |
| 70 | phenyl | C |
| 71 | 2-$NO_2$phenyl | C |
| 72 | 2-$CF_3$phenyl | C |
| 73 | 4-pyridyl | C |
| 74 | cyclopentyl | C |
| 75 | cyclohexyl | C |
| 76 | NH(cyclopentyl) | C |
| 77 | $N(Et)CH_2cycloPr$ | C |
| 78 | $NHCH(CH_3)CH_2CH_3$ | C |
| 79 | $NCH(CH_2CH_3)_2$ | C |
| 80 | $N(CH_2CH_2CH_3)_2$ | C |
| 81 | $N(CH_2CH_2OMe)CH_2CH_2CH_2OMe$ | C |
| 82 | $CH(CH_2CH_3)_2$ | D |
| 83 | $OCH(CH_2CH_3)_2$ | D |
| 84 | $N(CH_2CH_3)_2$ | D |
| 85 | $N(H)CH_2CH_2CH_3$ | D |
| 86 | $N(CH_2CH_2OCH_3)(CH_2CH_2CH_3)$ | D |
| 87 | $N(CH_2CH_3)CH_2CH_2CH_2CH_3$ | D |
| 88 | $NHCH(CH_2CH_3)CH_2SO_2Me$ | D |
| 89 | $N(CH_2CH_2OMe)_2$ | D |
| 90 | $N(Pr)CH_2cycloPr$ | D |
| 91 | $N(CH_2CH_3)CH_2SO_2Me$ | D |
| 92 | $CH(CO_2CH_2CH_3)_2$ | D |
| 93 | $CH(CH_2OCH_3)_2$ | D |
| 94 | 4-methoxyphenyl | D |
| 95 | morpholino | D |
| 96 | thiomorpholino | D |
| 97 | phenyl | D |
| 98 | 2-$NO_2$phenyl | D |
| 99 | 2-$CF_3$phenyl | D |
| 100 | 4-pyridyl | D |
| 101 | cyclopentyl | D |
| 102 | cyclohexyl | D |
| 103 | NH(cyclopentyl) | D |
| 104 | $N(Et)CH_2cycloPr$ | D |
| 105 | $NHCH(CH_3)CH_2CH_3$ | D |
| 106 | $NCH(CH_2CH_3)_2$ | D |
| 107 | $N(CH_2CH_2CH_3)_2$ | D |
| 108 | $N(CH_2CH_2OMe)CH_2CH_2CH_2OMe$ | D |
| 109 | $CH(CH_2CH_3)_2$ | E |
| 110 | $OCH(CH_2CH_3)_2$ | E |
| 111 | $N(CH_2CH_3)_2$ | E |
| 112 | $N(H)CH_2CH_2CH_3$ | E |
| 113 | $N(CH_2CH_2OCH_3)(CH_2CH_2CH_3)$ | E |
| 114 | $N(CH_2CH_3)CH_2CH_2CH_2CH_3$ | E |
| 115 | $NHCH(CH_2CH_3)CH_2SO_2Me$ | E |
| 116 | $N(CH_2CH_2OMe)_2$ | E |
| 117 | $N(Pr)CH_2cycloPr$ | E |
| 118 | $N(CH_2CH_3)CH_2SO_2Me$ | E |
| 119 | $CH(CO_2CH_2CH_3)_2$ | E |
| 120 | $CH(CH_2OCH_3)_2$ | E |
| 121 | 4-methoxyphenyl | E |
| 122 | morpholino | E |
| 123 | thiomorpholino | E |
| 124 | phenyl | E |
| 125 | 2-$NO_2$phenyl | E |
| 126 | 2-$CF_3$phenyl | E |
| 127 | 4-pyridyl | E |
| 128 | cyclopentyl | E |
| 129 | cyclohexyl | E |
| 130 | NH(cyclopentyl) | E |
| 131 | $N(Et)CH_2cycloPr$ | E |
| 132 | $NHCH(CH_3)CH_2CH_3$ | E |
| 133 | $NCH(CH_2CH_3)_2$ | E |
| 134 | $N(CH_2CH_2CH_3)_2$ | E |
| 135 | $N(CH_2CH_2OMe)CH_2CH_2CH_2OMe$ | E |
| 136 | $CH(CH_2CH_3)_2$ | F |
| 137 | $OCH(CH_2CH_3)_2$ | F |
| 138 | $N(CH_2CH_3)_2$ | F |
| 139 | $N(H)CH_2CH_2CH_3$ | F |
| 140 | $N(CH_2CH_2OCH_3)(CH_2CH_2CH_3)$ | F |
| 141 | $N(CH_2CH_3)CH_2CH_2CH_2CH_3$ | F |
| 142 | $NHCH(CH_2CH_3)CH_2SO_2Me$ | F |
| 143 | $N(CH_2CH_2OMe)_2$ | F |
| 144 | $N(Pr)CH_2cycloPr$ | F |
| 145 | $N(CH_2CH_3)CH_2SO_2Me$ | F |
| 146 | $CH(CO_2CH_2CH_3)_2$ | F |
| 147 | $CH(CH_2OCH_3)_2$ | F |
| 148 | 4-methoxyphenyl | F |
| 149 | morpholino | F |
| 150 | thiomorpholino | F |
| 151 | phenyl | F |
| 152 | 2-$NO_2$phenyl | F |
| 153 | 2-$CF_3$phenyl | F |
| 154 | 4-pyridyl | F |
| 155 | cyclopentyl | F |
| 156 | cyclohexyl | F |
| 157 | NH(cyclopentyl) | F |
| 158 | $N(Et)CH_2cycloPr$ | F |
| 159 | $NHCH(CH_3)CH_2CH_3$ | F |
| 160 | $NCH(CH_2CH_3)_2$ | F |
| 161 | $N(CH_2CH_2CH_3)_2$ | F |
| 162 | $N(CH_2CH_2OMe)CH_2CH_2CH_2OMe$ | F |
| 163 | $CH(CH_2CH_3)_2$ | G |

TABLE 2-continued

| | | |
|---|---|---|
| 164 | $OCH(CH_2CH_3)_2$ | G |
| 165 | $N(CH_2CH_3)_2$ | G |
| 166 | $N(H)CH_2CH_2CH_3$ | G |
| 167 | $N(CH_2CH_2OCH_3)(CH_2CH_2CH_3)$ | G |
| 168 | $N(CH_2CH_3)CH_2CH_2CH_2CH_3$ | G |
| 169 | $NHCH(CH_2CH_3)CH_2SO_2Me$ | G |
| 170 | $N(CH_2CH_2OMe)_2$ | G |
| 171 | $N(Pr)CH_2cycloPr$ | G |
| 172 | $N(CH_2CH_3)CH_2SO_2Me$ | G |
| 173 | $CH(CO_2CH_2CH_3)_2$ | G |
| 174 | $CH(CH_2OCH_3)_2$ | G |
| 175 | 4-methoxyphenyl | G |
| 176 | morpholino | G |
| 177 | thiomorpholino | G |
| 178 | phenyl | G |
| 179 | 2-$NO_2$phenyl | G |
| 180 | 2-$CF_3$phenyl | G |
| 181 | 4-pyridyl | G |
| 182 | cyclopentyl | G |
| 183 | cyclohexyl | G |
| 184 | NH(cyclopentyl) | G |
| 185 | $N(Et)CH_2cycloPr$ | G |
| 186 | $NHCH(CH_3)CH_2CH_3$ | G |
| 187 | $NCH(CH_2CH_3)_2$ | G |
| 188 | $N(CH_2CH_2CH_3)_2$ | G |
| 189 | $N(CH_2CH_2OMe)CH_2CH_2CH_2OMe$ | G |
| 190 | $CH(CH_2CH_3)_2$ | H |
| 191 | $OCH(CH_2CH_3)_2$ | H |
| 192 | $N(CH_2CH_3)_2$ | H |
| 193 | $N(H)CH_2CH_2CH_3$ | H |
| 194 | $N(CH_2CH_2OCH_3)(CH_2CH_2CH_3)$ | H |
| 195 | $N(CH_2CH_3)CH_2CH_2CH_2CH_3$ | H |
| 196 | $NHCH(CH_2CH_3)CH_2SO_2Me$ | H |
| 197 | $N(CH_2CH_2OMe)_2$ | H |
| 198 | $N(Pr)CH_2cycloPr$ | H |
| 199 | $N(CH_2CH_3)CH_2SO_2Me$ | H |
| 200 | $CH(CO_2CH_2CH_3)_2$ | H |
| 201 | $CH(CH_2OCH_3)_2$ | H |
| 202 | 4-methoxyphenyl | H |
| 203 | morpholino | H |
| 204 | thiomorpholino | H |
| 205 | phenyl | H |
| 206 | 2-$NO_2$phenyl | H |
| 207 | 2-$CF_3$phenyl | H |
| 208 | 4-pyridyl | H |
| 209 | cyclopentyl | H |
| 210 | cyclohexyl | H |
| 211 | NH(cyclopentyl) | H |
| 212 | $N(Et)CH_2cycloPr$ | H |
| 213 | $NHCH(CH_3)CH_2CH_3$ | H |
| 214 | $NCH(CH_2CH_3)_2$ | H |
| 215 | $N(CH_2CH_2CH_3)_2$ | H |
| 216 | $N(CH_2CH_2OMe)CH_2CH_2CH_2OMe$ | H |
| 217 | $CH(CH_2CH_3)_2$ | I |
| 218 | $OCH(CH_2CH_3)_2$ | I |
| 219 | $N(CH_2CH_3)_2$ | I |
| 220 | $N(H)CH_2CH_2CH_3$ | I |
| 221 | $N(CH_2CH_2OCH_3)(CH_2CH_2CH_3)$ | I |
| 222 | $N(CH_2CH_3)CH_2CH_2CH_2CH_3$ | I |
| 223 | $NHCH(CH_2CH_3)CH_2SO_2Me$ | I |
| 224 | $N(CH_2CH_2OMe)_2$ | I |
| 225 | $N(Pr)CH_2cycloPr$ | I |
| 226 | $N(CH_2CH_3)CH_2SO_2Me$ | I |
| 227 | $CH(CO_2CH_2CH_3)_2$ | I |
| 228 | $CH(CH_2OCH_3)_2$ | I |
| 229 | 4-methoxyphenyl | I |
| 230 | morpholino | I |
| 231 | thiomorpholino | I |
| 232 | phenyl | I |
| 233 | 2-$NO_2$phenyl | I |
| 234 | 2-$CF_3$phenyl | I |
| 235 | 4-pyridyl | I |
| 236 | cyclopentyl | I |
| 237 | cyclohexyl | I |
| 238 | NH(cyclopentyl) | I |
| 239 | $N(Et)CH_2cycloPr$ | I |
| 240 | $NHCH(CH_3)CH_2CH_3$ | I |
| 241 | $NCH(CH_2CH_3)_2$ | I |
| 242 | $N(CH_2CH_2CH_3)_2$ | I |
| 243 | $N(CH_2CH_2OMe)CH_2CH_2CH_2OMe$ | I |
| 244 | $CH(CH_2CH_3)_2$ | J |
| 245 | $OCH(CH_2CH_3)_2$ | J |
| 246 | $N(CH_2CH_3)_2$ | J |
| 247 | $N(H)CH_2CH_2CH_3$ | J |
| 248 | $N(CH_2CH_2OCH_3)(CH_2CH_2CH_3)$ | J |
| 249 | $N(CH_2CH_3)CH_2CH_2CH_2CH_3$ | J |
| 250 | $NHCH(CH_2CH_3)CH_2SO_2Me$ | J |
| 251 | $N(CH_2CH_2OMe)_2$ | J |
| 252 | $N(Pr)CH_2cycloPr$ | J |
| 253 | $N(CH_2CH_3)CH_2SO_2Me$ | J |
| 254 | $CH(CO_2CH_2CH_3)_2$ | J |
| 255 | $CH(CH_2OCH_3)_2$ | J |
| 256 | 4-methoxyphenyl | J |
| 257 | morpholino | J |
| 258 | thiomorpholino | J |
| 259 | phenyl | J |
| 260 | 2-$NO_2$phenyl | J |
| 261 | 2-$CF_3$phenyl | J |
| 262 | 4-pyridyl | J |
| 263 | cyclopentyl | J |
| 264 | cyclohexyl | J |
| 265 | NH(cyclopentyl) | J |
| 266 | $N(Et)CH_2cycloPr$ | J |
| 267 | $NHCH(CH_3)CH_2CH_3$ | J |
| 268 | $NCH(CH_2CH_3)_2$ | J |
| 269 | $N(CH_2CH_2CH_3)_2$ | J |
| 270 | $N(CH_2CH_2OMe)CH_2CH_2CH_2OMe$ | J |
| 271 | $CH(CH_2CH_3)_2$ | K |
| 272 | $OCH(CH_2CH_3)_2$ | K |
| 273 | $N(CH_2CH_3)_2$ | K |
| 274 | $N(H)CH_2CH_2CH_3$ | K |
| 275 | $N(CH_2CH_2OCH_3)(CH_2CH_2CH_3)$ | K |
| 276 | $N(CH_2CH_3)CH_2CH_2CH_2CH_3$ | K |
| 277 | $NHCH(CH_2CH_3)CH_2SO_2Me$ | K |
| 278 | $N(CH_2CH_2OMe)_2$ | K |
| 279 | $N(Pr)CH_2cycloPr$ | K |
| 280 | $N(CH_2CH_3)CH_2SO_2Me$ | K |
| 281 | $CH(CO_2CH_2CH_3)_2$ | K |
| 282 | $CH(CH_2OCH_3)_2$ | K |
| 283 | 4-methoxyphenyl | K |
| 284 | morpholino | K |
| 285 | thiomorpholino | K |
| 286 | phenyl | K |
| 287 | 2-$NO_2$phenyl | K |
| 288 | 2-$CF_3$phenyl | K |
| 289 | 4-pyridyl | K |
| 290 | cyclopentyl | K |
| 291 | cyclohexyl | K |
| 292 | NH(cyclopentyl) | K |
| 293 | $N(Et)CH_2cycloPr$ | K |
| 294 | $NHCH(CH_3)CH_2CH_3$ | K |
| 295 | $NCH(CH_2CH_3)_2$ | K |
| 296 | $N(CH_2CH_2CH_3)_2$ | K |
| 297 | $N(CH_2CH_2OMe)CH_2CH_2CH_2OMe$ | K |
| 271 | $CH(CH_2CH_3)_2$ | L |
| 272 | $OCH(CH_2CH_3)_2$ | L |
| 273 | $N(CH_2CH_3)_2$ | L |
| 274 | $N(H)CH_2CH_2CH_3$ | L |
| 275 | $N(CH_2CH_2OCH_3)(CH_2CH_2CH_3)$ | L |
| 276 | $N(CH_2CH_3)CH_2CH_2CH_2CH_3$ | L |
| 277 | $NHCH(CH_2CH_3)CH_2SO_2Me$ | L |
| 278 | $N(CH_2CH_2OMe)_2$ | L |
| 279 | $N(Pr)CH_2cycloPr$ | L |
| 280 | $N(CH_2CH_3)CH_2SO_2Me$ | L |
| 281 | $CH(CO_2CH_2CH_3)_2$ | L |
| 282 | $CH(CH_2OCH_3)_2$ | L |
| 283 | 4-methoxyphenyl | L |
| 284 | morpholino | L |
| 285 | thiomorpholino | L |
| 286 | phenyl | L |
| 287 | 2-$NO_2$phenyl | L |
| 288 | 2-$CF_3$phenyl | L |
| 289 | 4-pyridyl | L |
| 290 | cyclopentyl | L |
| 291 | cyclohexyl | L |
| 292 | NH(cyclopentyl) | L |
| 293 | $N(Et)CH_2cycloPr$ | L |
| 294 | $NHCH(CH_3)CH_2CH_3$ | L |

TABLE 2-continued

| 295 | NCH(CH$_2$CH$_3$)$_2$ | L |
| 296 | N(CH$_2$CH$_2$CH$_3$)$_2$ | L |
| 297 | N(CH$_2$CH$_2$OMe)CH$_2$CH$_2$CH$_2$OMe | L |

UTILITY

Compounds of this invention are expected to have utility in the treatment of inbalances associated with abnormal levels of CRF in patients suffering from depression, affective disorders, and/or anxiety.

CRF-R1 Receptor Binding Assay for the Evaluation of Bioloaical Activity

The following is a description of the isolation of cell membranes containing cloned human CRF-R1 receptors for use in the standard binding assay as well as a description of the assay itself.

Messenger RNA was isolated from human hippocampus. The MRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM MgCl$_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from $10^{-10}$–$10^{-5}$ M), 100 μl of $^{125}$I-ovine-CRF ($^{125}$I-o-CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980)], which provides Ki values for inhibition which are then used to assess biological activity.

A compound is considered to be active if it has a K$_i$ value of less than about 10000 nM for the inhibition of CRF.
Inhibition of CRF-Stimulated Adenylate Cyclase Activity Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6}$m) and 0.8 mg original wet weight tissue (approximately 40–60 mg protein). Reactions are initiated by the addition of 1 mM ATP/$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Bioloaical Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Dosaae and Formulation

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

CAPSULES

A large number of units capsules are prepared by filling standard two-piece hard gelatin capsules each with 100 mg of powdered active ingredient, 150 mg lactose, 50 mg cellulose, and 6 mg magnesium stearate.

SOFT GELATIN CAPSULES

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

TABLETS

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by:
LETTER PATENT of UNITED STATES is:

1. A compound of formula (I):

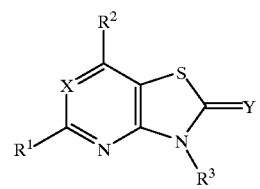

or a pharmaceutically acceptable salt thereof, wherein:

X is N;

Y is selected from the group: S, O and $NR^5$;

$R^1$ is selected from the group: H, $C_{1-4}$ alkyl, $C_{2-4}$ alkenyl, $C_{2-4}$ alkynyl, Cl, F, Br, I, —CN, $C_{1-5}$ haloalkyl, —$NR^6R^7$, —$NR^6COR^7$, —$OR^8$, —SH, and —$S(O)_nR^9$;

n is independently at each occurrence selected from the group: 0, 1, and 2;

$R^2$ is selected from the group: —$CR^{10}R^{11}R^{12}$, —$NR^{10a}R^{11a}$, —$NHCR^{10}R^{11}R^{12}$, —$OCR^{10}R^{11}R^{12}$, and phenyl, wherein the phenyl is substituted with 0–4 $R^a$;

$R^a$ is independently at each occurrence selected from the group: Cl, F, Br, I, $C_{1-4}$ haloalkyl, —$NO_2$, $C_{1-4}$ alkyl, $C_{2-5}$ alkenyl, $C_{2-4}$ alkynyl, $C_{3-7}$ cycloalkyl, $C_{2-5}$ carboalkoxy, SH, —$S(C_{1-4}$ alkyl), —CN, —OH, $C_{1-4}$ alkoxy, and —$NR^6R^7$, $OR^8$, $COR^7$;

$R^3$ is selected from the group: phenyl, pyridyl, pyrimidyl, napthyl, triazinyl, furanyl, quinolinyl, isoquinolinyl, thienyl, thiazolyl, pyrrolyl, oxazolyl, benzofuranyl, benzothienyl, benzothiazolyl, isoxazolyl, and pyrazolyl, and is substituted with 1 to 4 $R^b$ groups;

$R^b$ is independently at each occurrence selected from the group: $C_{1-6}$ alkyl, $C_{2-6}$ alkenyl, $C_{2-6}$ alkynyl, $C_{3-6}$ cycloalkyl, ($C_{3-8}$ cycloalkyl)$C_{1-4}$ alkyl-, $NO_2$, Cl, F, Br, I, —CN, $C_{1-6}$ haloalkyl, —$NR^{14}R^{15}$, —$NR^8COR^{14}$, —$NR^8CO_2R^{14}$, —$COR^{14}$, —$OR^{14}$, —$CONR^{14}R^{15}$, —$CO_2R^{14}$, —SH, and —$S(O)_nR^{14}$;

$R^5$ is —$CO(C_{1-4}$ alkyl) or —$CO_2(C_{1-4}$ alkyl);

$R^6$ and $R^7$ independently at each occurrence selected from the group: H, $C_{1-4}$ alkyl, and $C_{3-6}$ cycloalkyl;

$R^8$ is independently at each occurrence selected from the group: H, $C_{1-4}$ alkyl, $C_{1-4}$ haloalkyl, and $C_{3-6}$ cycloalkyl;

$R^9$ is independently at each occurrence selected from the group: $C_{1-4}$ alkyl, $C_{1-4}$ haloalkyl, and aryl;

$R^{10}$ and $R^{11}$ are independently at each occurrence selected from the group: $C_{1-6}$ alkyl, $C_{2-6}$ alkenyl, $C_{2-6}$ alkynyl, $C_{3-8}$ cycloalkyl, ($C_{3-8}$ cycloalkyl)$C_{1-4}$ alkyl-, —$(CH_2)_n$aryl, —$(CH_2)_n$heteroaryl, ($C_{1-6}$ alkoxy)$C_{1-6}$ alkyl-, —$C_{0-6}$—CN, —$NH(C_{1-6}$ alkyl), and —$N(C_{1-6}$ alkyl)$_2$, each $R^{10}$ and $R^{11}$ being optionally substituted with 0–3 $R^c$;

$R^c$ is independently at each occurrence selected from the group: F, =O, $C_{1-4}$ alkyl, $C_{1-4}$ haloalkyl, $C_{2-4}$ alkenyl, $C_{2-4}$ alkynyl, $C_{1-4}$ alkoxy, —CN, $S(O)_nC_{1-4}$ alkyl, $NH_2$, $NH(C_{1-4}$ alkyl), $N(C_{1-4}$ alkyl)$_2$, phenyl, pyridyl, and pyrimidyl;

$R^{12}$ is independently at each occurrence selected from the group: H, $C_{1-6}$ alkyl; alternatively, $R^{10}$ and $R^{11}$ are taken together, along with the interconnected carbon, to form a 4–8 membered saturated or partially saturated carbocyclic ring substituted with 0–2 $R^e$ or a 4–8 membered saturated or partially saturated heterocyclic ring containing 1–2 heteroatoms selected from O, N, $NR^8$, and S and substituted with 0–2 $R^d$;

$R^d$ is independently at each occurrence selected from the group: =O, $C_{1-4}$ alkyl, $C_{1-4}$ haloalkyl, $C_{2-2}$ alkenyl, $C_{2-4}$ alkynyl, $C_{1-4}$ alkoxy, —CN, —S(O)$_n C_{1-4}$ alkyl, —NH$_2$, —NH($C_{1-4}$ alkyl), —N($C_{1-4}$ alkyl)$_2$, and phenyl;

$R^{10a}$ and $R^{11a}$ are independently at each occurrence selected from the group: $C_{1-6}$ alkyl, $C_{2-6}$ alkenyl, $C_{2-6}$ alkynyl, ($C_{3-8}$ cycloalkyl)$C_{1-4}$ alkyl-, —(CH$_2$)$_n$aryl, —(CH$_2$)$_n$hetero-aryl, ($C_{1-6}$ alkoxy)$C_{1-6}$ alkyl-, —$C_{1-6}$—CN, —NH($C_{1-6}$ alkyl), —N($C_{1-6}$ alkyl)$_2$, S(O)$_n R^8$, C(O)$_{1-2} R^8$, and C(O)NR$^6 R^7$ each $R^{10a}$ being substituted with 0–3 $R^c$; alternatively, $R^{10a}$ and $R^{11a}$ are taken together, along with the interconnected nitrogen, to form a 4–8 membered saturated or partially saturated heterocyclic ring containing 0–1 additional heteroatoms selected from O, N, NR$^8$, and S and substituted with 0–3 $R^e$;

$R^{14}$ and $R^{15}$ are independently at each occurrence selected from the group: H, $C_1$–$C_4$ alkyl, $C_1$–$C_4$ haloalkyl, $C_3$–$C_6$ cycloalkyl, ($C_{3-8}$ cycloalkyl)C1–4 alkyl-, aryl, —($C_1$–$C_4$ alkyl)aryl, heteroaryl and —($C_1$–$C_4$) heteroaryl;

aryl is phenyl substituted with 0–3 $R^e$;

$R^e$ is independently selected at each occurrence from the group: $C_{1-4}$ alkyl, $C_{2-4}$ alkenyl, $C_{2-5}$ alkynyl, $C_{3-6}$ cycloalkyl, —NO$_2$, Cl, F, Br, I, —CN, $C_{1-4}$ haloalkyl, —NH$_2$, —NH($C_{1-4}$ alkyl), —N($C_{1-4}$ alkyl)$_2$, OR$^{14}$, S(O)$_n R^{14}$; and, heteroaryl is independently at each occurrence selected from the group: pyridyl, pyrimidinyl, triazinyl, furanyl, thienyl, imidazolyl, indolyl, pyrrolyl, oxazolyl, benzofuranyl, isoxazolyl and pyrazolyl substituted with 0–3 $R^e$.

2. A compound according to claim 1, wherein:

Y is S or O;

$R^1$ is selected from the group: H, $C_{1-4}$ alkyl, $C_{2-4}$ alkenyl, $C_{2-4}$ alkynyl, Cl, F, —CN, $C_{1-5}$ haloalkyl, and —NR$^6 R^7$;

$R^3$ is selected from the group: phenyl, pyridyl, and pyrimidyl, and is substituted with 1 to 4 $R^b$ groups; and, $R^b$ is independently at each occurrence selected from the group: $C_{1-10}$ alkyl, $C_{2-10}$ alkenyl, $C_{2-10}$ alkynyl, $C_{3-6}$ cycloalkyl, ($C_{3-8}$ cycloalkyl)$C_{1-4}$ alkyl-, NO$_2$, Cl, F, —CN, $C_{1-4}$ haloalkyl, —NR$^{14} R^{15}$, —NR$^8$COR$^{14}$, —NR$^8$CO$_2 R^{14}$, —COR$^{14}$, —OR$^{14}$, —CONR$^{14} R^{15}$, —CO$_2 R^{14}$, —SH, and —S(O)$_n R^{14}$.

3. A compound according to claim 1, wherein the compound is selected from the group:

3-(2-Bromo-4-isopropyl)phenyl-7-(N-cyclopropylmethyl-N-propyl)amino-5-methylthiazolo[4,5-d]pyrimidin-2-thione;

3-(2-Bromo-4-isopropyl)phenyl-7-(N,N-diethylamino)-5-methyl-thiazolo[4,5-d]pyrimidin-2-thione;

7-(N,N-bismethoxyethylamino)-3-(2-bromo-4-isopropyl)phenyl-5-methylthiazolo[4,5-d]pyrimidin-2-thione;

3-(2-Bromo-4-isopropyl)phenyl-7-(N-butyl-N-ethyl)amino-5-methylthiazolo[4,5-d]pyrimidin-2-thione;

3-(2-Bromo-4-isopropyl)phenyl-7-(N,N-di-sec-butylamine)-5-methylthiazolo[4,5-d]pyrimidin-2-thione;

7-(N, N-diethylamino)-5-methyl-3-(2,4,6-trimethyl)phenylthiazolo[4,5-d]pyrimidin-2-thione;

7-(N,N-bismethoxyethylamino)-5-methyl-3-(2,4,6-trimethyl)phenylthiazolo[4,5-d]pyrimidin-2-thione;

7-(N-cyclopropylmethyl-N-propyl)-5-methyl-3-(2,4,6-trimethyl)phenylthiazole[4,5-d]pyrimidin-2-thione;

3-(2-Bromo-4-isopropyl)phenyl-7-(N-cyclopropylmethyl-N-propyl)amino-5-methylthiazolo[4,5-d]pyrimidin-2-one;

7-(N,N-bismethoxyethylamino)-3-(2-bromo-4-isopropyl)phenyl-5-methylthiazolo[4,5-]pyrimidin-2-one;

3-(N,N-diethylamino)-5-methylthiazolo[4,5-d]pyrimidin-2-one;

7-(N,N-diethylamino)-5-methyl-3-(2,4,6-trimethyl)phenylthiazolo[4,5-d]pyrimidin-2-one;

7-(N,N-bismethoxyethylamino)-5-methyl-3-(2,4,6-trimethyl)phenylthiazolo[4,5-d]pyrimidin-2-one; and, 7-(N-cyclopropylmethyl-N-propyl)amino-5-methyl-3-(2,4,6-trimethyl)phenylthiazolo[4,5-d]pyrimidin-2-one;

or a pharmaceutically acceptable salt form thereof.

4. A pharmaceutical composition, comprising: a pharmaceutically acceptable carrier and a therapeutically effective amount of a compound according to claim 1, or a pharmaceutically acceptable salt form thereof.

5. A method of treating psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, in a mammal, comprising: administering to the mammal a therapeutically effective amount of a compound of claim 1 or a pharmaceutically acceptable salt form thereof.

* * * * *